United States Patent [19]

Esteve Soler

[11] 4,146,636
[45] Mar. 27, 1979

[54] 2,5-DIHYDROXY BENZENE SULPHONIC ACIDS FOR SCALP TREATMENT

[76] Inventor: José Esteve Soler, Via Augusta 244, Barcelona, Spain

[21] Appl. No.: 790,882

[22] Filed: Apr. 26, 1977

[30] Foreign Application Priority Data

May 11, 1976 [FR] France ................... 76 14113

[51] Int. Cl.² ................... A61K 31/28; A61K 31/295; A61K 31/315
[52] U.S. Cl. .................... 424/287; 424/289; 424/294; 424/295
[58] Field of Search ............... 424/287, 289, 294, 295

[56] References Cited
PUBLICATIONS

Schmidt–Chem. Abst. vol. 27 (1933), p. 13639.

*Primary Examiner*—Sam Rosen
*Attorney, Agent, or Firm*—Armand P. Boisselle

[57] ABSTRACT

The invention relates to new salts of 2,5-dihydroxy benzene sulphonic acids and the process for their production.

The new compounds according to the invention are salts corresponding to the general formula (I):

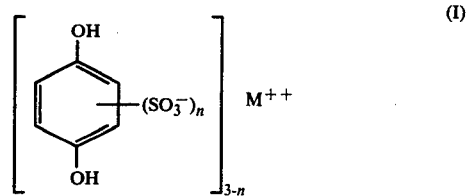

in which
$M^{++}$ represents the divalent cation of a transition metal,
n is the number 1 or 2, but with the proviso that, when n is the number 2, the two radicals $-SO_3^-$ are situated in the para-position relative to one another.

The new compounds are useful for treating disorders of the scalp.

3 Claims, No Drawings

2,5-DIHYDROXY BENZENE SULPHONIC ACIDS FOR SCALP TREATMENT

This invention relates to new salts of 2,5-dihydroxy benzene sulphonic acids, to the process for their production and to their use in treatment of the scalp.

The new compounds according to the invention are salts corresponding to the following general formula:

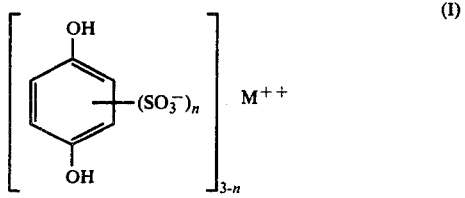

in which
$M^{++}$ represents the divalent cation of a transition metal,
n is the number 1 or 2, but with the proviso that, when n is 2, the two radicals $-SO_3^-$ are situated in the para-position relative to one another,
and the hydrated salts, especially the salts containing two molecules of water of crystallisation.

The preferred compounds of the invention are those of general formula I in which the transition metal M is selected from iron, copper, zinc and cadmium.

Accordingly, these preferred compounds of the invention correspond to general formulae I-a and I-b below:

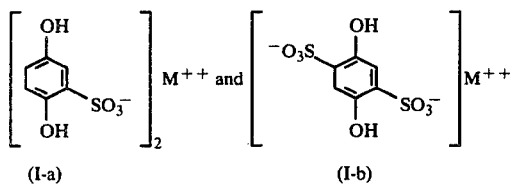

The invention also relates to a process for producing the new compounds corresponding to general formula I, in which:

(a) a benzene sulphonic acid corresponding to the general formula

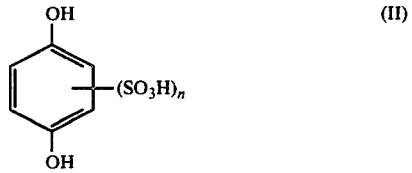

in which n is the number 1 or 2 and, when n is 2, the two radicals $-SO_3^-$ are situated in the para-position relative to one another, is reacted with a divalent salt or hydroxide of a transition metal M, or (b) a double decomposition reaction is carried out between a first salt of a transition metal M and a second salt of the benzene sulphonic acid of formula II of a different metal.

It will be recalled that dandruff is generally caused by the normally fatty desquamation of the scalp. It is clear that there is a close relationship between the appearance of dandruff and the loss of hair. The fatty desquamation of the scalp is the cause of the appearance of lipids of which the depilatory properties, however rarely discussed, would nevertheless appear to be beyond doubt.

The auto-oxidation of these lipids causes dandruff and, hence, loss of hair. The use of antioxidants such as hydroquinone, resorcinol and pyrocatechol to retard this auto-oxidation process has long been known.

The salts of 2,5-dihydroxy benzene sulphonic acids according to the present invention have excellent antioxidant properties and have been found to be of considerable interest in the treatment of various disorders of the scalp and particularly in the treatment of dandruff.

The present invention also relates to new pharmaceutical preparations containing as active principle at least one compound corresponding to general formula I above. These pharmaceutical preparations are intended in particular for the treatment of seborrhoeic dermatitis, parakeratosis and pityriasis of the scalp.

The production of the new compounds according to the invention is illustrated by the following Examples:

EXAMPLE 1

Cadmium 2,5-dihydroxy benzene-1,4-disulphonate 27 g (0.1 mole) of 2,5-dihydroxy benzene-1,4-disulphonic acid recrystallised from ethanol are dissolved in 200 ml of distilled water. 19 g (0.11 mole) of cadmium carbonate are then added, followed by stirring for about 5 hours at ambient temperature. The slight excess of cadmium carbonate is then filtered, followed by evaporation to dryness and oven-drying for 8 hours at a temperature of approximately 80° C.

A water-soluble white-grey product, which is cadmium 2,5-dihydroxy benzene-1,4-disulphonate containing 2 molecules of water of crystallisation, is thus obtained in a yield of 40.5 g.

The infrared spectrum recorded with pellets of KBr gives maximums at the following frequencies: 3500, 3220, 1620, 1510, 1420, 1195, 1110, 1025, 895, 885, 820 and 650 cm$^{-1}$.

EXAMPLE 2

Cadmium 2,5-dihydroxy benzene sulphonate 38.0 g (0.2 mole) of 2,5-dihydroxy benzene sulphonic acid recrystallised from ethanol are dissolved in 250 ml of distilled water. 19 g (0.11 mole) of cadmium carbonate are added, followed by stirring at ambient temperature for about 3 hours. The excess cadmium carbonate is filtered, followed by evaporation to dryness and oven-drying for 8 hours at a temperature of approximately 80° C.

A water-soluble white-pink product, which is cadmium 2,5-dihydroxy benzene sulphonate containing 2 molecules of water of crystallisation, is thus obtained in a yield of 51 g.

The infrared spectrum recorded with pellets of KBr gives maximums at the following frequencies: 3310, 1630, 1520, 1450, 1380, 1190, 1085, 1025, 940, 865, 825, 790, 760 and 715 cm$^{-1}$.

EXAMPLE 3

Zinc 2,5-dihydroxy benzene-1,4-disulphonate 27 g (0.1 mole) of 2,5-dihydroxy benzene-1,4-disulphonic acid recrystallised from ethanol are dissolved in 200 ml of distilled water. 14 g (0.11 mole) of zinc carbonate ($ZnCO_3$) are added, followed by stirring at ambient temperature for about 5 hours. The excess zinc carbonate is filtered, followed by evaporation to dryness and oven-drying for 8 hours at a temperature of approximately 80° C.

A water-soluble white product, which is zinc 2,5-dihydroxy benzene-1,4-disulphonate containing 2 molecules of water of crystallisation, is thus obtained in a yield of 35.5 g.

The infrared spectrum recorded with pellets of KBr gives maximums at the following frequencies: 3470, 3220, 1620, 1510, 1420, 1195, 1110, 1025, 895, 885, 820 and 655 cm$^{-1}$.

EXAMPLE 4

Zinc 2,5-dihydroxy benzene sulphonate 38.0 g (0.2 mole) of 2,5-dihydroxy benzene sulphonic acid recrystallised from ethanol are dissolved in 250 ml of distilled water. 14 g (0.11 mole) of zinc carbonate ($ZnCO_3$) are added, followed by stirring at ambient temperature for about 4 hours. The excess zinc carbonate is filtered, followed by evaporation to dryness and oven-drying for 8 hours at a temperature of approximately 85° C.

A yellowish water-soluble product, which is zinc 2,5-dihydroxybenzene sulphonate containing 2 molecules of water of crystallisation, is thus obtained in a yield of 44.5 g.

The infrared spectrum recorded with pellets of KBr gives maximums of the following frequencies: 3320, 1620 1520, 1450, 1375, 1190, 1085, 1025, 940, 860, 825, 790, 760 and 715 cm$^{-1}$.

EXAMPLE 5

Copper 2,5-dihydroxy benzene-1,4-disulphonate 5.4 g (0.02 mole) of 2,5-dihydroxy benzene-1,4-disulphonic acid recrystallised from ethanol are dissolved in 50 ml of distilled water. 2.43 g (0.011 mole) of basic copper carbonate are then added, followed by stirring at ambient temperature for about 4 hours. The slight excess of basic copper carbonate is filtered, followed by evaporation to dryness and oven-drying for 8 hours at a temperature of approximately 80° C.

A brown water-soluble product, which is copper 2,5-dihydroxy benzene-1,4-disulphonate containing 2 molecules of water of crystallisation, is thus obtained in a yield of 6.9 g.

The infrared spectrum recorded with pellets of KBr gives maximums at the following frequencies: 3210, 1430, 1200, 1110, 1025, 890, 875, 820 and 660 cm$^{-1}$.

EXAMPLE 6

Copper 2,5-dihydroxy benzene sulphonate 7.6 g (0.04 mole) of 2,5-dihydroxy benzene sulphonic acid recrystallised from ethanol are dissolved in 60 ml of distilled water. 2.43 g (0.011 mole) of basic copper carbonate are then added, followed by stirring at ambient temperature for about 7 hours. The slight excess of basic copper carbonate is filtered, followed by evaporation to dryness and oven-drying for 8 hours at a temperature of approximately 80° C.

A brown water-soluble product, which is copper 2,5-dihydroxy benzene sulphonate containing 2 molecules of water of crystallisation, is thus obtained in a yield of 9.5 g.

The infrared spectrum recorded with pellets of KBr gives maximums at the following frequencies: 3310, 1520, 1450, 1380, 1180, 1085, 1025, 940, 865, 825, 795 and 715 cm$^{-1}$.

EXAMPLE 7

Iron 2,5-dihydroxy benzene-1,4-disulphonate 3.2 g (0.01 mole) of calcium 2,5-dihydroxy benzene-1,4-disulphonate are dissolved in 30 ml of distilled water. 3.0 g (0.011 mole) of hydrated ferrous sulphate are then added, followed by stirring at ambient temperature for about 3 hours. The calcium sulphate formed is filtered, followed by evaporation to dryness and oven-drying for 8 hours at a temperature of approximately 80° C.

A grey-blue water-soluble product, which is iron 2,5-dihydroxy benzene-1,4-disulphonate containing 2 molecules of water of crystallisation, is thus obtained in a yield of 3.4 g.

The infrared spectrum recorded with pellets of KBr gives maximums at the following frequencies: 3400, 1625, 1420, 1200, 1110, 1025, 890, 820 and 655 cm$^{-1}$.

EXAMPLE 8

Iron 2,5-dihydroxy benzene sulphonate 8.36 g (0.02 mole) of calcium 2,5-dihydroxy benzene sulphonate are dissolved in 70 ml of distilled water. 6.1 g (0.022 mole) of hydrated ferrous sulphate are then added, followed by stirring at ambient temperature for about 4 hours. The calcium sulphate formed is filtered, followed by evaporation to dryness and oven-drying for 8 hours at a temperature of approximately 85° C.

A grey water-soluble product, which is iron 2,5-dihydroxy benzene sulphonate containing 2 molecules of water of crystallisation, is thus obtained in a yield of 9.1 g.

The infrared spectrum recorded in pellets of KBr gives maximums at the following frequencies: 3480, 1625, 1510, 1335, 1190, 1085, 1030, 885, 820 and 790 cm$^{-1}$.

The high solubility and stability in water and alcohol of the new compounds according to the present invention enables them to be incorporated in various types of cosmetic preparations, such as lotions, shampoos, creams, etc., which are useful for the treatment of hair and the scalp.

In the cosmetic and/or pharmaceutical compositions according to the invention, isopropanol, n-propanol, a water-in-oil emulsion, polyvinyl pyrrolidone, etc., may be used for example as support or vehicle.

In addition, the cosmetic and/or pharmaceutical compositions according to the invention may be enriched by the addition of vitamins, vegetable extracts, bactericides, etc.

It is pointed out that the active principle, namely the new compounds according to the invention, for example cadmium or zinc 2,5-dihydroxy benzene-1,4-disulphonate, should be present in a proportion which is compatible with its activity and its tolerance. In general, the proposed doses are of the order of 1 to 5% by weight, the ideal dose being approximately 2%.

The pharmacodynamic properties of the new salts according to the invention are shown in the following with reference to the particular examples of cadmium 2,5-dihydroxy benzene-1,4-disulphonate and zinc 2,5-dihydroxy benzene-1,4-disulphonate.

Local tolerance on the conjunctiva of rabbits:

Comparative tests are carried out with:

(a) cadmium 2,5-dihydroxy benzene-1,4-disulphonate in the form of a 1% solution in distilled water
(b) cadmium 2,5-dihydroxy benzene-1,4-disulphonate in the form of a 2% solution in distilled water
(c) cadmium 2,5-dihydroxy benzene-1,4-disulphonate in the form of a 2.5% solution in distilled water
(d) cadmium 2,5-dihydroxy benzene-1,4-disulphonate in the form of a 5% solution in distilled water
(e) zinc 2,5-dihydroxy benzene-1,4-disulphonate in the form of a 1% solution in distilled water
(f) zinc 2,5-dihydroxy benzene-1,4-disulphonate in the form of a 2% solution in distilled water
(g) zinc 2,5-dihydroxy benzene-1,4-disulphonate in the form of a 2.5% solution in distilled water
(h) zinc 2,5-dihydroxy benzene-1,4-disulphonate in the form of a 5% solution in distilled water.

The degrees of ocular irritation are quantified in accordance with "Federal Register" 37, No. 83, Apr. 28, 1972, page 191, 12.

The irritation observed has a degree of 1 or at the very most a degree of 2 and is always temporary. This evaluation concerns the palpebral conjunctiva and indicates that some vessels are lightly injected.

| Product tested | Number of rabbits with positive irritation Group I (5 mins.) | | Number of rabbits with positive irritation Group II (24 h) | |
|---|---|---|---|---|
| | 1 h | 24 h | 24 h | 48 h |
| a) | 4/5 | 0/5 | 0/5 | 0/5 |
| b) | 2/5 | 0/5 | 0/5 | 0/5 |
| c) | 5/5 | 1/5 | 1/5 | 0/5 |
| d) | 5/5 | 1/5 | 1/5 | 1/5 |
| e) | 0/6 | 0/6 | 0/6 | 0/6 |
| f) | 2/6 | 0/6 | 0/6 | 0/6 |
| g) | 1/6 | 0/6 | 0/6 | 0/6 |
| h) | 3/6 | 0/6 | 0/6 | 0/6 |

The action on the ocular conjunctiva of rabbits of cadmium 2,5-dihydroxy benzene-1,4-disulphonate and zinc 2,5-dihydroxy benzene-1,4-disulphonate in the concentrations of 1%, 2%, 2.5% and 5%, qualifies as negative irritation.

The following formulation Examples illustrate the cosmetic and/or pharmaceutical application of the new compounds according to the invention.

EXAMPLE A (Alcoholic capillary lotion)

| | By weight |
|---|---|
| Cadmium 2,5-dihydroxy benzene-1,4-disulphonate | 2.0% |
| Isopropanol | 50.0% |
| Perfume | 0.2% |
| Distilled water | 47.8% |
| | 100.0% |

EXAMPLE B (Liquid for treating hair)

| | By weight |
|---|---|
| Cadmium 2,5-dihydroxy benzene-1,4-disulphonate | 2.0% |
| Calcium pantothenate | 0.5% |
| Ethanol | 70.0% |
| Isopropyl myristate | 10.0% |
| Perfume | 0.4% |
| Distilled water | 17.1% |
| | 100.0% |

EXAMPLE C (Shampoo)

| | By weight |
|---|---|
| Cadmium 2,5-dihydroxy benzene-1,4-disulphonate | 2.0% |
| Triethanolamine lauryl sulphate | 10.0% |
| Lauryl diethylamine oxide | 10.0% |
| Cocomonoethanolamide | 5.0% |
| Ethanol | 10.0% |
| Distilled water | 63.0% |
| | 100.0% |

EXAMPLE D (Shampoo)

| | By weight |
|---|---|
| Cadmium 2,5-dihydroxy benzene-1,4-disulphonate | 2.0% |
| Triethanolamine lauryl sulphate | 13.0% |
| Sodium lauryl ether sulphate | 33.0% |
| Lauric monoisopropanolamide | 1.5% |
| Distilled water | 50.5% |
| | 100.0% |

EXAMPLE E (Alcoholic capillary lotion)

| | By weight |
|---|---|
| Zinc 2,5-dihydroxy benzene-1,4-disulphonate | 1.0-2.0% |
| Isopropanol | 50.0% |
| Perfume | 0.2% |
| Distilled water | 47.8% |
| | 100.0% |

EXAMPLE F (Liquid for treating hair)

| | By weight |
|---|---|
| Zinc 2,5-dihydroxy benzene-1,4-disulphonate | 1.0-2.0% |
| Calcium pantothenate | 0.5% |
| Ethanol | 70.0% |
| Isopropyl myristate | 10.0% |
| Perfume | 0.4% |
| Distilled water | 17.1% |
| | 100.0% |

EXAMPLE G (Shampoo)

| | By weight |
|---|---|
| Zinc 2,5-dihydroxy benzene-1,4-disulphonate | 1.0-2.0% |
| Triethanolamine lauryl sulphate | 10.0% |
| Lauryl diethylamine oxide | 10.0% |
| Cocomonoethanolamide | 5.0% |
| Ethanol | 10.0% |
| Distilled water | 63.0% |
| | 100.0% |

EXAMPLE H (Shampoo)

| | By weight |
|---|---|
| Zinc 2,5-dihydroxy benzene-1,4-disulphonate | 1.0-2.0% |
| Lauryl sulphate triethanolamine | 13.0% |
| Sodium lauryl ether sulphate | 33.0% |
| Lauric monoisopropanolamide | 1.5% |
| Distilled water | 50.5% |
| | 100.0% |

EXAMPLE I (Emulsion shampoo)

| | By weight |
|---|---|
| Zinc 2,5-dihydroxy benzene-1,4-disulphonate | 1.0% |
| Lactic acid | 0.2% |
| 2-Bromo-2-nitropropane-1,3-diol (bronol) | 0.03% |
| Disodium EDTA salt | 0.02% |
| Coco derivative of sodium methyl laurate (24% solution) | 20.5% |
| Coco derivative of sodium isethionate (83% solution) | 15.5% |
| 5% aqueous solution of Veegum H.V. | 20.0% |
| Ethylene glycol monostearate | 1.0% |
| Ethoxylated lanoline alcohols | 0.5% |
| Polyethoxylated oleic alcohol | 1.5% |
| Diethanolamide of coconut fatty acids | 2.5% |
| Steari-ammonium pentaoxyethyl chloride (20% solution) | 3.75% |
| Distill water q.s.f. | 100.0% |

I claim:

1. A method for the treatment of dandruff, seborrhoeic dermatitis, parakeratosis and pityriasis of the scalp which comprises applying to the scalp, an effective amount of at least one salt corresponding to the general formula (I):

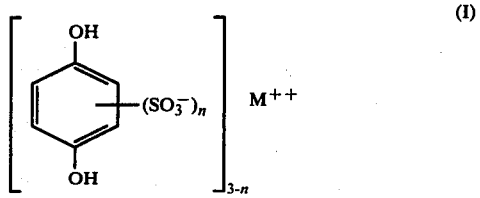

in which $M^{++}$ represents the divalent cation of a transition metal, n is a number selected from 1 and 2, with the proviso that, when n is 2, the two radicals —$SO_3^-$ are situated in the para-position relative to one another, including the hydrated salts.

2. A method according to claim 1 wherein the salts of the general formula (I) contain two molecules of water of crystallization.

3. A method as claimed in claim 1, wherein the salts of general formula (I) are selected from the group consisting of:

cadmium 2,5-dihydroxy benzene-1,4-disulphonate;
cadmium 2,5-dihydroxy benzene sulphonate;
zinc 2,5-dihydroxy benzene-1,4-disulphonate;
zinc 2,5-dihydroxy benzene sulphonate;
copper 2,5-dihydroxy benzene-1,4-disulphonate;
copper 2,5-dihydroxy benzene sulphonate;
iron 2,5-dihydroxy benzene-1,4-disulphonate;
iron 2,5-dihydroxy benzene sulphonate.

* * * * *

UNITED STATES PATENT AND TRADEMARK OFFICE
CERTIFICATE OF CORRECTION

PATENT NO. : 4,146,636
DATED : March 27, 1979
INVENTOR(S) : José Esteve Soler

It is certified that error appears in the above-identified patent and that said Letters Patent are hereby corrected as shown below:

On the title page, between the items "Inventor" and "Application No." add the item --Assignee: Investigacion, Procedimentos & Marcas, S.A. "Inpromsa", Barcelona, Spain --.

Signed and Sealed this

Twenty-third Day of October 1979

[SEAL]

Attest:

RUTH C. MASON
Attesting Officer

LUTRELLE F. PARKER
Acting Commissioner of Patents and Trademarks